US009349198B2

(12) United States Patent
Claus et al.

(10) Patent No.: US 9,349,198 B2
(45) Date of Patent: May 24, 2016

(54) ROBUST ARTIFACT REDUCTION IN IMAGE RECONSTRUCTION

(71) Applicant: General Electric Company, Schenectady, NY (US)

(72) Inventors: Bernhard Erich Hermann Claus, Niskayuna, NY (US); David Allen Langan, Clifton Park, NY (US); Taylor Robert Braun-Jones, Boston, MA (US)

(73) Assignee: General Electric Company, Niskayuna, NY (US)

(*) Notice: Subject to any disclaimer, the term of this patent is extended or adjusted under 35 U.S.C. 154(b) by 291 days.

(21) Appl. No.: 13/952,444

(22) Filed: Jul. 26, 2013

(65) Prior Publication Data

US 2015/0029178 A1    Jan. 29, 2015

(51) Int. Cl.
G06K 9/00      (2006.01)
G06T 11/00     (2006.01)
A61B 6/03      (2006.01)
A61B 6/00      (2006.01)

(52) U.S. Cl.
CPC .............. G06T 11/005 (2013.01); A61B 6/032 (2013.01); A61B 6/5258 (2013.01); G06T 2200/04 (2013.01)

(58) Field of Classification Search
CPC .............. G06T 7/0012; G06T 2200/04; G06T 2207/30052
USPC ........................................ 382/154, 131, 100
See application file for complete search history.

(56) References Cited

U.S. PATENT DOCUMENTS

| | | | |
|---|---|---|---|
| 7,372,935 B2 | 5/2008 | Bernhardt et al. | |
| 7,660,450 B2 | 2/2010 | Van De Haar et al. | |
| 7,711,083 B2 | 5/2010 | Heigl et al. | |
| 8,410,448 B2 | 4/2013 | Forthmann et al. | |
| 2009/0097612 A1 | 4/2009 | Rauch | |
| 2009/0297011 A1 | 12/2009 | Brunner et al. | |
| 2011/0081071 A1 | 4/2011 | Benson et al. | |
| 2012/0237115 A1 | 9/2012 | Rohkohl et al. | |
| 2013/0070991 A1* | 3/2013 | Yang ................. | A61B 6/5258 382/131 |

OTHER PUBLICATIONS

De Man et al, "Reduction of metal streak artifacts in x-ray computed tomography using a transmission maximum a posteriori algorithm", IEEE, 2000.*

Meilinger et al., "Metal artifact reduction in CBCT using forward projected reconstruction information and mutual information re alignment", World Congress on Medical Physics and Biomedical Engineering, pp. 46-49, vol. 25, 2009.

Amirkhanov et al., "Projection-Based Metal-Artifact Reduction for Industrial 3D X-ray Computed Tomography", IEEE, pp. 2193-2202, vol. 17, Issue 12, Dec. 2011.

* cited by examiner

Primary Examiner — Ruiping Li
(74) Attorney, Agent, or Firm — Melissa K. Dobson

(57) ABSTRACT

Approaches are disclosed for removing or reducing metal artifacts in reconstructed images. The approaches include creating a metal mask in the projection domain, interpolating data within the metal mask, and perform a reconstruction using the interpolated data. In certain embodiments the metal structure is separately reconstructed and combined with the reconstructed volume.

15 Claims, 7 Drawing Sheets

ROBUST ARTIFACT REDUCTION IN IMAGE RECONSTRUCTION

BACKGROUND

Embodiments of the invention generally relate to imaging, and more particularly to the reduction of artifacts in reconstructed images.

In modern medicine, medical professionals routinely conduct patient imaging examinations to assess the internal tissue of a patient in a non-invasive manner. Furthermore, for industrial applications related to security or quality control, screeners may desire to non-invasively assess the contents of a container (e.g., a package or a piece of luggage) or the internal structure of a manufactured part. Accordingly, for medical, security, and industrial applications, X-ray imaging techniques may be useful for noninvasively characterizing the internal composition of a subject of interest.

In certain instances, X-ray images may suffer from artifacts due to the X-rays being unable to penetrate through the imaged volume or otherwise suffering from poor penetration and/or scatter attributable to structures within the imaged volume. For example, metallic objects in the field of view (such as tools, metal implants, screws, pins, stents, or other metallic objects present in the patient) may lead to data irregularities (e.g., artifacts) due to the X-rays not penetrating through the object, penetrating in low quantities, and/or scattering of the X-rays directed at the metallic object.

Further, certain types of image acquisitions, such as certain types of C-arm acquisitions, may impose limitations that limit the ability of the system to address such data imperfections. For example, mobile C-arm systems may be useful in many imaging contexts, but may also be associated with limited angle acquisition, small number of views, image truncation, limited quantitative resolution, limited penetration, and so forth. As a result, images reconstructed from imperfect data collected on such systems may have limited capability to address various types of image artifacts, such as those artifacts attributable to the metal object(s) within the patient.

BRIEF DESCRIPTION

In one embodiment, a computer-implemented method for processing projection image data is provided. The method comprises the act of generating a set of tentative two-dimensional (2D) metal masks. Each tentative 2D metal mask is generated based on a comparison between a respective projection image and a corresponding background image. Each tentative 2D metal mask is backprojected to generate a respective set of backprojected three-dimensional (3D) data in image space for each tentative 2D metal mask. The sets of backprojected three-dimensional (3D) data are combined in image space to generate a 3D metal mask. The 3D metal mask is reprojected to generate one or more metal masks in projection space.

In another embodiment, a computer-implemented method for processing projection image data is provided. The method comprises the act of accessing a mathematically incomplete set of acquired projection images. An initial volume is reconstructed from the mathematically incomplete set of acquired projection images. A three-dimensional (3D) metal mask is generated from the initial volume. The 3D metal mask is refined. The 3D metal mask is reprojected to generate one or more metal masks in projection space.

In a further embodiment, an image processing system is provided. The image processing system comprises a memory storing one or more routines and a processing component configured to execute the one or more routines stored in the memory. The one or more routines, when executed by the processing component, cause acts to be performed comprising: accessing or acquiring projection image data; generating a set of tentative two-dimensional (2D) metal masks, wherein each tentative 2D metal mask is generated based on a comparison between a respective projection image and a corresponding background image; backprojecting each tentative 2D metal mask to generate a respective set of backprojected three-dimensional (3D) data in image space for each tentative 2D metal mask; combining the sets of backprojected three-dimensional (3D) data in image space to generate a 3D metal mask; and reprojecting the 3D metal mask to generate one or more metal masks in projection space.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present disclosure relates to approaches that may be employed to reduce image artifacts, such as approaches for metal artifact reduction (MAR), in the reconstruction of volumetric images from X-ray projection images.

As discussed herein, the present approaches may be applicable in circumstances where acquired projection data is impacted by high-density regions or objects, such as metal objects, that affect transmission of X-rays through the imaged volume. Such circumstances may arise in various X-ray imaging contexts, such as C-arm acquisition, mobile C-arm, and computed tomography (CT) contexts. The present approaches may help address issues where X-ray penetration and transmission is impacted by the presence of metal objects within the imaged volume. Metal structures within the imaged volume often lead to streak artifacts in the reconstructed volumetric images, due to beam-hardening, partial volume effects, noise, etc. These streaks can negatively impact even regions of the images that are far away from the location of the metal structures, and limit the clinical value of the image data. Many conventional approaches address this problem in the context of CT where acquired data is generally of excellent quality. In many contexts, however, there may be additional limitations in the quality of the acquired data, such as data truncation (some parts of the imaged object may be present/visible in the projections only for a part of the scan), incomplete data (projection data is available only for less than a "full spin", i.e., less than 180 degree plus fan angle; and/or a relatively wide angular spacing of about 1 degree or more between consecutive views), low penetration (e.g., due to a low-power X-ray source or long path lengths through the imaged object for some view angles), and limited geometric accuracy (e.g., due to vibration or other factors in the gantry motion). Such data limitations and differential X-ray penetration and transmission may lead to artifacts. The present robust approaches help address certain of the issues noted above.

The approaches discussed herein use a 3D metal mask (i.e., a map of metal locations in the reconstructed 3D volume) and a corresponding set of 2D metal masks (i.e., a map of the metal objects within each of the projection images). As noted above, limitations in the quality of the data collected with the imaging systems may make the generation of an accurate metal mask difficult. As discussed herein, the current approaches allow a metal mask to be identified using robust and computationally efficient processing steps, thereby enabling high-quality reconstructions, with significantly reduced impact due to metal in the field of view. In addition, the present approaches outline strategies to re-insert more meaningful metal structures into the 3D volume, thereby improving clinical value of the data.

Figure 1:
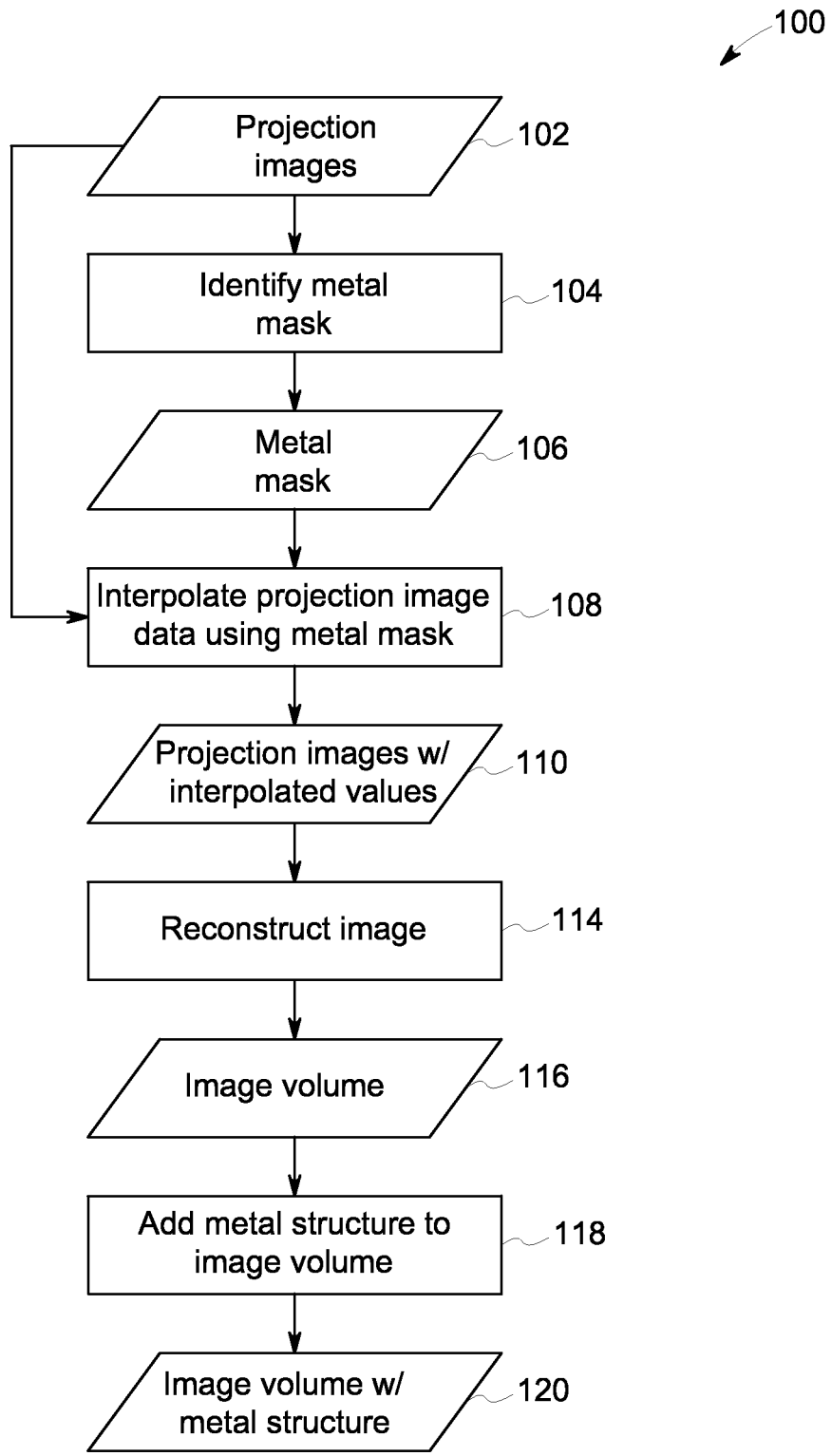
FIG. 1 depicts a generalized flowchart describing algorithmic steps for processing projection images to generate a volume having reduced metal artifacts, in accordance with aspects of the present disclosure.

For example, turning to FIG. 1, in one implementation, a sequence of steps may be performed in which: a metal mask 106 is identified (block 104) in a set of acquired projection images 102; projection image data 102 is interpolated (block 108) using the metal mask 106; an image reconstruction process (block 114) is performed on the interpolated projection images 110 to generate an image volume 116 that is free or substantially free of metal; and a metal structure is added (block 118) to the image volume 116. These steps are discussed in more detail below following a brief description of a suitable imaging system that may be used for acquiring and processing image data as discussed herein.

Figure 2:
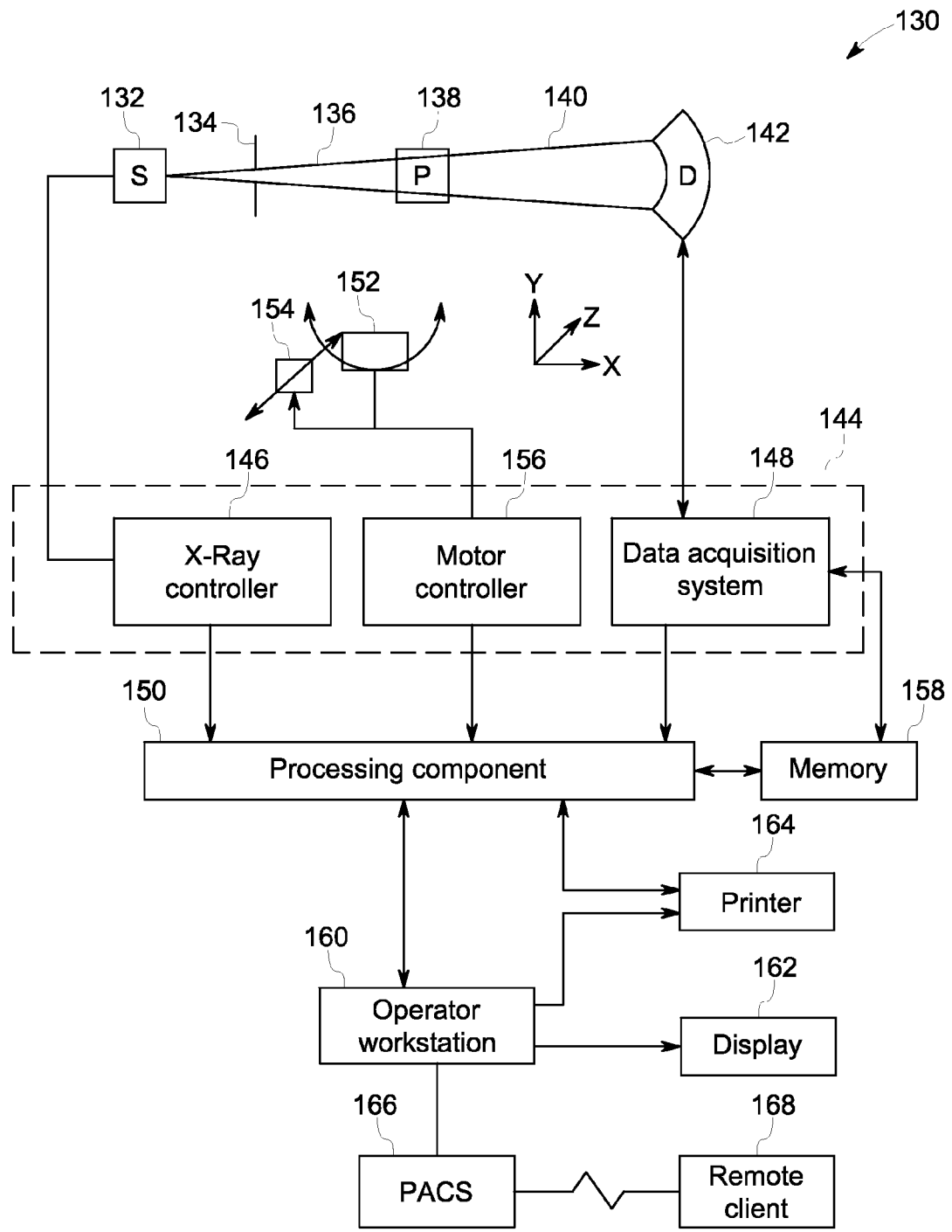
FIG. 2 is a diagrammatical view of a C-arm or CT imaging system for use in producing images, in accordance with aspects of the present disclosure.

With this in mind, an example of an imaging system 130, such as a C-arm or computed tomography (CT) system, suitable for use with the present artifact reduction approaches is depicted in FIG. 2. Though a C-arm system is discussed with respect to FIG. 2, it should be appreciated that the system 130 and discussion related to C-arm imaging is provided merely to facilitate explanation by providing one example of a particular imaging context. However, the present approach is not limited to C-arm or CT implementations and, indeed may be used in various other suitable imaging contexts where metal artifact or other artifacts may be present.

Turning back to FIG. 2, in the depicted example, the imaging system 130 is designed to acquire X-ray attenuation data at a variety of view angles around a patient (or other subject or object of interest). In the embodiment illustrated in FIG. 1, imaging system 130 includes a source of X-ray radiation 132 positioned adjacent to a collimator 134. The X-ray source 132 may be an X-ray tube, a distributed X-ray source (such as a solid-state or thermionic X-ray source) or any other source of X-ray radiation suitable for the acquisition of medical or other images.

The collimator 134 permits a shaped beam of X-rays 136 to pass into a region in which a patient 138, is positioned. In the depicted example, the X-rays 136 are collimated, such as into a fan-shaped or a cone-shaped beam that passes through the imaged volume. A portion of the X-ray radiation 140 passes through or around the patient 138 (or other subject of interest) and impacts a detector array, represented generally at reference numeral 142. Detector elements of the array produce electrical signals that represent the intensity of the incident X-rays 140. These signals are acquired and processed to reconstruct images of the features within the patient 138.

Source 132 is controlled by a system controller 144, which furnishes both power, and control signals for examination sequences. In the depicted embodiment, the system controller 144 controls the source 132 via an X-ray controller 146 which may be a component of the system controller 144. In such an embodiment, the X-ray controller 146 may be configured to provide power and timing signals to the X-ray source 132.

Moreover, the detector 142 is coupled to the system controller 144, which controls acquisition of the signals generated in the detector 142. In the depicted embodiment, the system controller 144 acquires the signals generated by the detector using a data acquisition system 148. The data acquisition system 148 receives data collected by readout electronics of the detector 142. The data acquisition system 148 may receive sampled analog signals from the detector 142 and convert the data to digital signals for subsequent processing by a processor 150 discussed below. Alternatively, in other embodiments the digital-to-analog conversion may be performed by circuitry provided on the detector 142 itself. The system controller 144 may also execute various signal processing and filtration functions with regard to the acquired image signals, such as for initial adjustment of dynamic ranges, interleaving of digital image data, and so forth.

In the embodiment illustrated in FIG. 2, system controller 144 is coupled to a rotational subsystem 152. A linear positioning subsystem 154 may also be present in certain contexts, such as where the system 130 is a CT system. The rotational subsystem 152 enables the X-ray source 132, collimator 134 and the detector 142 to be rotated one or multiple turns around the patient 138, such as rotated primarily in an x,y-plane about the patient (where the z-axis refers to the long axis of the patient). In some embodiments, system constraints may limit rotation in the x,y-plane, such as to less than 220 degrees or some other suitable limited rotational range. Other motions of the C-arm are possible as well. It should be noted that the rotational subsystem 152 might include a gantry or C-arm upon which the respective X-ray emission and detection components are disposed. Thus, in such an embodiment, the system controller 144 may be utilized to operate the gantry or C-arm.

The linear positioning subsystem 154, when present, may enable the patient 138, or more specifically a table supporting the patient, to be displaced, such as in the z-direction relative to rotation of the gantry or C-arm. Thus, the table may be linearly moved (in a continuous or step-wise fashion) to generate images of particular areas of the patient 138. In the depicted embodiment, the system controller 144 controls the movement of the rotational subsystem 152 and/or the linear positioning subsystem 154 via a motor controller 156. While the preceding discussion generalizes aspects of the various rotational and linear positioning systems that may be present, other positioning systems may be present and/or the linear or rotational positioning systems may include respective subsystems. For example, one or more robotic arms may be present that are employed in positioning operations. Similarly, an independent positioner subsystem for the source 132 and detector 142 may be present, a manual motion positioner may be present, a stationary source 132 and detector 142 may be employed, and/or a rotational stage may be provided for the imaged object such that the object may be rotated during imaging. Further, combinations of these elements, or hybrid systems may be employed having various combinations of such positioning systems and subsystems.

In general, system controller 144 commands operation of the imaging system 130 (such as via the operation of the source 132, detector 142, and positioning systems described above) to execute examination protocols and to process acquired data. For example, the system controller 144, via the systems and controllers noted above, may rotate a gantry or C-arm supporting the source 132 and detector 142 about a subject of interest so that X-ray attenuation data may be obtained at a variety of views relative to the subject. In the present context, system controller 144 may also include signal processing circuitry, associated memory circuitry for storing programs and routines executed by the computer (such as routines for executing artifact reduction techniques described herein), as well as configuration parameters, image data, and so forth.

In the depicted embodiment, the image signals acquired and processed by the system controller 144 are provided to a processing component 150 for reconstruction of images. The processing component 150 may be one or more conventional microprocessors. The data collected by the data acquisition system 148 may be transmitted to the processing component 150 directly or after storage in a memory 158. Any type of memory suitable for storing data might be utilized by such an exemplary system 130. For example, the memory 158 may include one or more optical, magnetic, and/or solid state memory storage structures. Moreover, the memory 158 may be located at the acquisition system site and/or may include remote storage devices for storing data, processing parameters, and/or routines for artifact reduction, as described below.

The processing component 150 may be configured to receive commands and scanning parameters from an operator via an operator workstation 160, typically equipped with a keyboard and/or other input devices. An operator may control the system 130 via the operator workstation 160. Thus, the operator may observe the reconstructed images and/or otherwise operate the system 130 using the operator workstation 160. For example, a display 162 coupled to the operator workstation 160 may be utilized to observe the reconstructed images and to control imaging. Additionally, the images may also be printed by a printer 164 which may be coupled to the operator workstation 160.

Further, the processing component 150 and operator workstation 160 may be coupled to other output devices, which may include standard or special purpose computer monitors and associated processing circuitry. One or more operator workstations 160 may be further linked in the system for outputting system parameters, requesting examinations, viewing reconstructed images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 160 may also be coupled to a picture archiving and communications system (PACS) 166. PACS 166 may in turn be coupled to a remote client 168, radiology department information system (RIS), hospital information system (HIS) or to an internal or external network, so that others at different locations may gain access to the raw or processed image data.

While the preceding discussion has treated the various exemplary components of the imaging system 130 separately, these various components may be provided within a common platform or in interconnected platforms. For example, the processing component 150, memory 158, and operator workstation 160 may be provided collectively as a general or special purpose computer or workstation configured to operate in accordance with the aspects of the present disclosure. In such embodiments, the general or special purpose computer may be provided as a separate component with respect to the data acquisition components of the system 130 or may be provided in a common platform with such components. Likewise, the system controller 144 may be provided as part of such a computer or workstation or as part of a separate system dedicated to image acquisition.

With the foregoing discussion of a suitable implementation of a C-arm or CT imaging system 130 in mind, the following provides an example of one implementation of a present approach that may be used to address artifacts attributable to metal present in the imaged volume. Turning back to FIG. 1, in this example, a set of projection images 102 acquired by an X-ray imaging system, such as system 130 of FIG. 2, is initially processed to identify (block 104) a metal mask 106 for each projection image. That is, the goal in this step is to identify the region (i.e., the metal mask 106 or metal trace) in the projection images 102 that contain metal (with other, non-metal regions in the context of this discussion being referred to as "background"). This step is followed by an interpolation step 108, where the data values within the identified metal regions are replaced in the projection images by appropriately determined values, followed by a reconstruction step 114, where a "metal-free" 3D volume 116 is constructed from the interpolated projection data. Metal structures are added (block 118) to the reconstructed 3D volume 116 obtained in step 114 to generate an image volume with metal structures included 120. These steps 104 through 118 are discussed in more detail herein below.

In step 104, where the metal mask 106 in the projection images 102 is identified, selecting a region or regions (i.e., mask or masks 106) that are too large or too small may have a negative impact on the achieved image quality. For example, if the mask 106 is defined or identified as being larger than necessary, image information that does not contain metal is replaced by interpolated values (in step 108, discussed below), thereby limiting reconstruction detail in the corresponding region of the reconstructed 3D volume. Conversely, if the mask 106 is identified or defined so as not to encompass the portion of the image corresponding to metal, residual pixels containing (high-contrast) metal remain in the image, thereby causing residual streaks in the reconstructed volume. Therefore it is useful to obtain an accurate metal mask 106, with no or few pixels that are incorrectly classified.

Further, it is worth noting that certain of the strategies discussed herein for creating the metal masks 106 are based on the assumption that pixels that don't show a relatively high-attenuation signal are unlikely to cause streak artifacts in the final reconstructed image, even though they may in fact correspond to locations with metal present in the beam. Therefore, in certain implementations, more emphasis may be placed on detecting "metal pixels" than on removing all "background pixels" from the metal mask 106. Similarly, the focus of certain implementations is less on correctly identifying metal regions with high accuracy and more on identifying regions in the projection images 102 that are located "close to" image regions occupied by metal objects that are likely to create streak artifacts in the reconstructed image. For example, even if the outline of a metal object is only roughly identified through the processing, any high-attenuation pixels that are close to the metal object may then be added to the metal mask 106, thereby minimizing their contribution to streak artifacts in the image.

Figure 3:
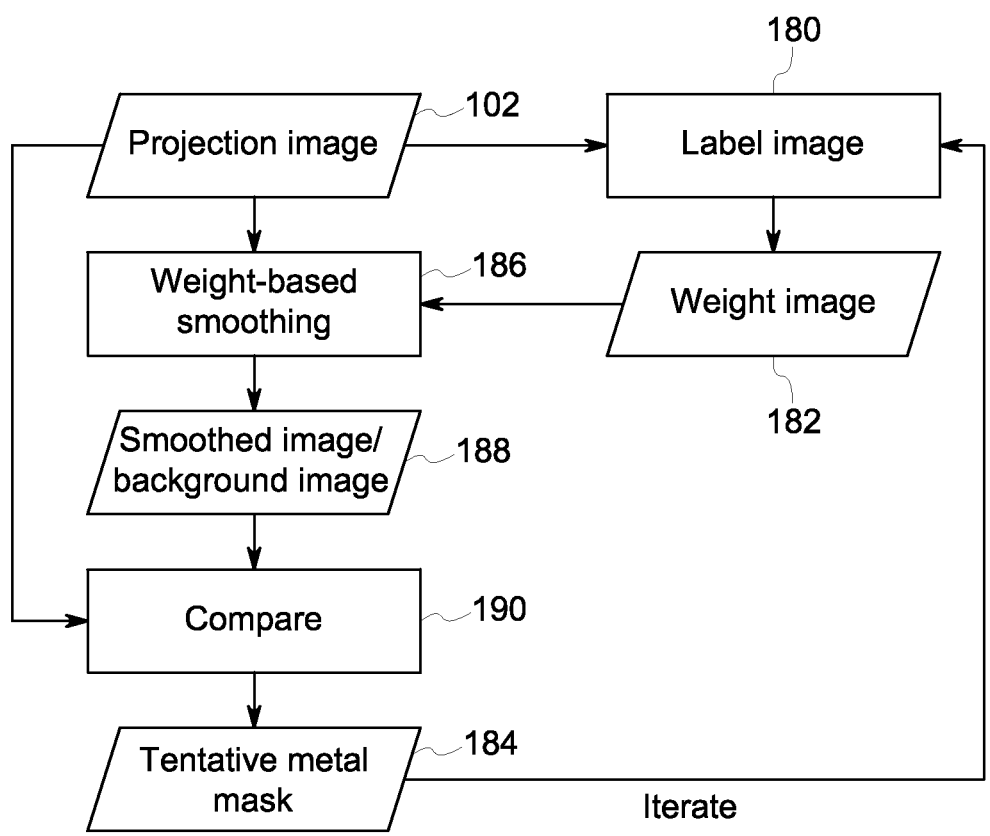
FIG. 3 depicts a flowchart describing algorithmic steps for generating a tentative metal mask, in accordance with aspects of the present disclosure.

In a first implementation, a tentative metal mask 184 is generated. By way of example, turning to FIG. 3, a generalized approach for generating a tentative metal mask 184 using weight-based smoothing is provided. In this example, projection images 102 are initially provided. A label image 180 is provided, and may initially be set to arbitrary or specified values, such as all 1's (which may represent the initial assumption that all pixel data in the image is valid). For another example, in one embodiment, in the projection domain prior knowledge or thresholding approaches may be used to identify regions corresponding to non-valid data (such as due to the collimator blades being projected onto the detector or other previously known metal effects) in the projection images 102. Based on the label map and the projection image a smoothed image is generated, representing an estimate of the background (i.e., image values representative of non-metal regions). Note that the background image assumes values everywhere in the image plane, even in regions where in fact metal is present. Assuming some minimum level of attenuation by a metal object that is in the imaged space, projection data 102 can be compared against the estimated background image, and can be classified (i.e., labeled) as "metal" where the attenuation is larger than the local background attenuation plus some delta ($\Delta$) value.

In the depicted example, the label image 180 is used to derive a weight image 182 (e.g., an image or map having corresponding weight values, such as from 0 to 1, at each corresponding pixel location of the respective projection image 102) that provides a weight (such as a 0 or 1 in a binary context or in a range from 0 to 1 in a continuous weight context) on a pixel-by-pixel basis with respect to the respective projection image 102. For example, in a binary weight image context a weight of 1 may be assigned to pixels believed to correspond to valid (e.g., non-metal) image background while a weight of 0 may be assigned to pixels believed to correspond to regions that are not believed to depict an image background region (e.g., metal or collimator regions).

The current weight image 182 may in turn be used to perform a weight-based smoothing operation (block 186). In one implementation, the weight-based smoothing operation 186 may include multiplying, on a pixel-by-pixel basis, the current weight image 182 for an iteration with the respective projection image 102 and applying a smoothing filter or kernel to the result to generate a smoothed or background image 188 where, in one embodiment, each pixel location is an estimate of the local background, i.e., not containing any metal regions. The resulting background image 188 contains a local average of the smoothed image in the "valid-data" regions (i.e., regions labeled as background), and an interpolation or extrapolation of the smoothed valid data into the non-valid data regions (i.e., regions labeled as metal).

It should also be noted that a smoothing operation (using the same or a different smoothing operator or kernel) may also be applied to the weight image 182 at each iteration to generate a smoothed weight image. The smoothed weight image may in turn be used to normalize the background image, such as by dividing (on a pixel-by-pixel basis) the background image by the smoothed weight image. The result of such a normalization step is a smoothed and/or interpolated background image 188 in the present context. In one example, the smoothing filter may consist of a simple convolution with a simple averaging-type kernel, e.g., a Gaussian, or a box-car filter with square footprint, or other suitable filter. In certain implementations, the smoothing filter can be chosen to be a separable filter, i.e., it can be implemented, for example, as a pair of 1D filters (where one 1D filter operates along the rows of the image, the other operates along the columns of the image). The result of this smoothing and normalization with the smoothed weight image is a smoothed projection image that, in the present context, corresponds to the image background.

As will be appreciated, and returning to the comparison step 190, a global constant may not be useful as a threshold value (e.g., due to varying path lengths through the imaged object as a function of view angle, and/or for different locations within each projection image), and instead it may be useful to at least compare local projection image values against the local background, when available in deriving and updating the label image 180.

In the depicted example, the derived background image 188 may be compared (block 190) to the respective projection image 102 and a tentative metal mask 184 derived based on the comparison. In one implementation, due to varying degrees of X-ray penetration, focal spot and detector blurring, and so forth, it may be useful to adapt the comparison thresholds (i.e., the delta ($\Delta$) over background) as a function of the background signal level. In one example, the contrast of metal structures over the background may be smaller in regions of the image where X-ray penetration is good compared to high attenuation regions. This effect may be managed, in one implementation, by choosing a locally varying threshold, e.g., by using a monotonic (e.g., linear) relationship between the locally estimated background (which is indicative of the level of "penetration", i.e., the fraction of X-rays that reach the detector) and the applied threshold. In one embodiment, a hybrid rule may be used, e.g., with a constant threshold in good penetration regions and a threshold dependent on the local penetration for regions with less penetration. Based on the comparison between the respective projection image 102 and the corresponding background image 188, a tentative metal mask 184 is generated for the respective projection image.

Since a one-pass approach to generating a tentative label mask may still be influenced by the impact of metal pixels in the generation of the background image, in one embodiment the tentative metal mask 184 may in turn be used to update the label image 180 (i.e., to label pixels as metal or not metal based on this initial assessment) and the process iterated until a completion criteria is met (e.g., a specified number of iterations or some threshold degree of difference between successive tentative metal masks 184). Thresholds in the comparison may be adapted for this optional iterative update. Upon completion of the iteration cycle, the tentative metal mask 184 may be used in subsequent processes, discussed below.

Figure 4:
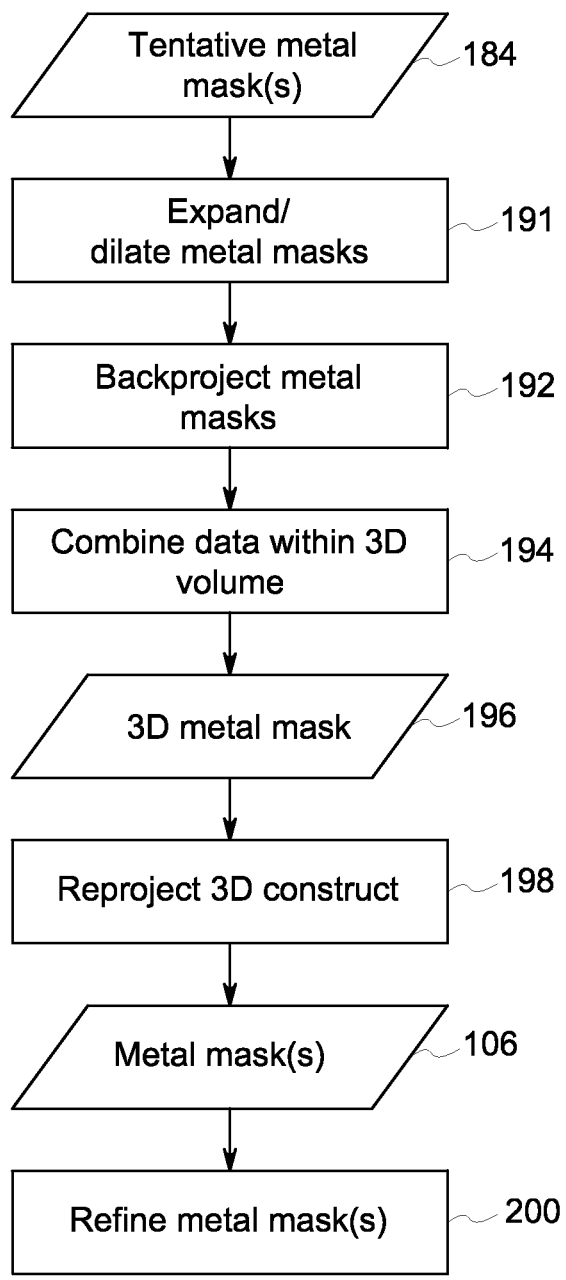
FIG. 4 depicts a flowchart depicting algorithmic steps for generating metal masks, in accordance with aspects of the present disclosure.

Turning to FIG. 4, in one implementation the tentative, two-dimensional metal mask(s) 184 derived from the respective projection images 102 are combined in three-dimensional space and refined to form the metal mask(s) 106. In the depicted example, a projection-based approach for identifying the metal mask 106 (as described herein above) may be combined with a consolidation step in the 3D domain (i.e., the image or spatial domain). In one embodiment, the tentative metal masks 184 are backprojected (block 192) into the imaged volume. Prior to this backprojection step 192, the tentative metal masks 184 may undergo expansion and/or dilation processing (block 191). The backprojection step 192 may be followed by a local combination (block 194) of the backprojection output within the 3D volume. In one embodiment, in the backprojection step information is collected at each voxel indicating, for example, how many backprojected views show valid data at this location, how many views show the presence of a metal object (i.e., the corresponding pixel in the projection view is labeled as "metal"), etc. Through this combination step 194 the information from the backprojection step is used to obtain 3D metal mask 196 based on the individual tentative metal masks 184. A final step in the consolidation of the tentative metal masks 184 is the reprojection (block 198) of the 3D metal mask 196, thereby creating a sequence of 2D metal masks 106 in the projection domain. The metal masks 106 may, in turn, be refined (block 200), as discussed herein.

An analysis may be performed, as part of the combination (block 194) of data in the 3D volume, on a voxel-by-voxel basis (and based on the information collected during the backprojection step 192) whether a given voxel should be labeled as a metal voxel or a background voxel. In circumstances where the tentative metal masks 184 contain no errors or flaws, for example, if only a single projection image indicates "not metal" for a voxel, then that voxel would not be labeled as "metal", or, conversely, only if all projection images indicate "metal" at a corresponding location (i.e., if the result is "unanimous") will a voxel be labeled as "metal". While this is one example, in other embodiments, non-unanimous voting schemes may be employed such that complete agreement among all projection images need not be obtained in designating a voxel as "metal" (or "not-metal", depending on the implementation).

In one implementation, errors or flaws in the tentative metal masks 184 may be addressed as part of this analysis in the combination step 194. For example, there may be pixels in the tentative metal masks 184 that should have been labeled as "metal" but which were not correctly captured by the algorithm e.g., due to noise, due to interpolation, and so forth. To accommodate such errors in the tentative metal masks 184, a rule may be designed (as part of combination step 194) for classifying a voxel as "metal" or "background" in such a manner that a voxel is labeled "metal" if a majority or threshold percentage (i.e., >x %) of projection images 102 indicates "metal" at that location. In one embodiment, this combination step is implemented as a thresholding operation, where the threshold may be locally varying based on various aspects of the collected information during the backprojection (e.g., penetration, number of views with valid data, etc.). In one embodiment, the threshold is a fixed percentage x of the total number of acquired projection views.

As will be appreciated, lowering the threshold makes the process more robust to noise, but at the cost of increasing the probability of obtaining false positives (i.e., voxels that are erroneously labeled as "metal"). For example, bone surfaces (e.g., vertebrae endplates) are likely to have a high "metal-like" attenuation in the views where the projection direction is tangential to the bone surface, and therefore they are likely to be erroneously labeled as "metal" in the corresponding tentative metal masks 184. If the fraction of projection views 102 that experiences these long path lengths through the bone (at corresponding locations) is high enough, the associated regions in 3D will be erroneously labeled as "metal", an outcome which becomes more likely as the voting threshold, x, is lowered.

Another effect of lowering the threshold is that metal objects may have an associated "halo", where locations or regions in the 3D volume near the metal object are superimposed with the metal object in a relatively large number of views. In such a situation, at a given voxel, an erroneously large number of votes for "metal" may result from the 3D combination. This effect essentially scales with the size of the metal object (i.e., the "halo" gets generally bigger for bigger metal objects). In the special case where multiple metal objects may be superimposed in a subset of views (e.g., multiple metal objects intersecting the same axial slice, for an axial spin), the halos of the two objects may combine such that a region between the objects may be erroneously labeled as "metal". For these reasons it may be desirable to leave the voting threshold relatively high, thereby achieving some robustness to noise while limiting detrimental effects like halos.

In certain embodiments, another processing step or adjustment may consist of only considering or counting projection views with good penetration in a local context (i.e., a relatively small line-integral along the ray-paths) in at least part of a neighborhood, thereby precluding the noisiest portion of the views from contributing to the determination (i.e., only projection views having suitable noise characteristics in a local region of interest are counted in the "voting" scheme). Such an approach allows a larger threshold to be set for the "metal" decision in the 3D volume, since the views with the noisiest contribution are excluded from the determination process. A consequence of this approach, however, is that a certain angular range of projection views may be excluded from the voting scheme due to noise considerations, and the shape of the 3D metal mask may become distorted through this "limited-angle" effect. Thus, it may be desirable to balance these factors when employing such an implementation. In one embodiment, the areas in a projection image 102 with good penetration (i.e., low noise) can be identified by examining the signal level of the respective projection image (or the derived background image 188), and the local threshold, x, in the 3D image domain may be chosen relative to the total number of views where the respective location is part of a "good penetration" region.

In a further refinement, metallic structures outside of the central (generally cylindrical) field of view may be addressed. For example, in one implementation the processing may include managing regions of the volume that are not always within the field of view of the projection images 102. In this case, the reconstruction problem is typically referred to as "reconstruction from truncated projections". In such circumstances, determination thresholds (e.g., voting thresholds) may be set relative to the number of projections that actually "see" the corresponding location in 3D, and not relative to the total number of views. Such an implementation may help in avoiding streaks due to metal structures that are outside of the field of view during part of the acquisition.

Further to address situations where geometric alignment is not perfect, other processing steps may be performed to facilitate implementation of a suitable scheme for determining whether a voxel is metal or not (e.g., a voting scheme). For example, in the case where there is some degree of geometric misalignment, for small metal structures the backprojected projection image information may not properly align, and at any given location within the 3D volume 196 only a subset of backprojected views may be indicative of "metal", even in situations where the tentative metal maps 184 were in agreement (i.e., the structure was correctly labeled as "metal" in all projection images). Depending on the specified voting threshold, such a small metal structure may not become a part of the 3D metal mask 196. For larger metal structures, the resulting 3D metal masks 196 may be smaller than they should be in reality. One approach to address this geometric misalignment problem is to dilate (block 191) the tentative metal masks 184 before backprojecting (block 192) and determining metal/non-metal voxels, thereby artificially enlarging the 3D metal mask 196 and ensuring a larger overlap region in the 3D volume.

It should be noted that the combination of tentative metal maps 184 in a 3D volumetric image may also be performed using more sophisticated approaches than the voting rules approach as discussed here. For example, the tentative metal masks 184 may be associated with an estimate of associated probability or confidence. If the confidence in a label (i.e., "metal" or "background") is high, the impact on the combined 3D metal mask 196 may be higher than if the confidence is low. In one example, the voting scheme as discussed above is augmented by a weighting (or confidence) factor, and the local threshold is applied relative to the local sum of confidence weights.

In summary, the approach as discussed here provides a means for generating a 3D metal mask 196 that is robust with respect to a number of aspects that may negatively impact the data quality. For example, as discussed herein a binary voting scheme may be employed (i.e., a scheme where votes are only to whether metal is present (e.g., a weight of "1") at a voxel or absent (e.g., a weight of "0"), with no further weighting or confidence taken into consideration. Such a scheme may not take in to account the presence of data truncation (e.g., "how many views contribute to this voxel") and/or penetration (e.g., "where does the view contribute, but not have meaningful signal"). However, other voting schemes discussed herein may take into account such data issues as well as other considerations. For example, in a generalized sense a weighting scheme may be employed, such as a confidence weighting scheme in determining whether a voxel should be classified as metal or not. As discussed herein, this may be accomplished by determining the confidence-weighted sum of back-projected tentative metal masks at each voxel location and the sum of backprojected confidence-weights at each voxel location in order to determine a ratio at each voxel that may then be used in characterizing each voxel as metal or not. At one extreme, such a scheme may be employed in a binary implementation, where the confidence weights are 0 or 1. Alternatively, the confidence-weights for each projection may be derived from one or more of (a) the local penetration/signal level in the associated background image, (b) the degree of confidence in a tentative metal label, (c) prior knowledge of collimator position within the respective projection image, (d) knowledge about data points being invalid in certain areas of the image (where in one embodiment regions that fall outside of the image (or active detector area) may be also considered as non-valid, thereby addressing regions in the volume that are not "seen" by all projection views), and so forth. In such implementations, a voxel may be characterized as metal if the ratio of confidence-weighted sum of back-projected tentative metals masks and the sum of confidence weights exceeds a specified threshold (e.g., 0.6, 0.7, 0.8, and so forth) that is typically less than 1.0.

Once a 3D metal mask 196 is generated, it may be mapped into the projection domain by reprojecting (block 198). In this way, a metal mask 106 can be defined in each of the projection images 102. As discussed in greater detail below, the initial identification of the metal mask 106 may be followed by additional suitable steps (i.e., refinement steps 200), such as a dilation of the metal mask 106 and/or additional clean-up to refine the metal mask 106, as discussed in greater detail below.

Figure 5:
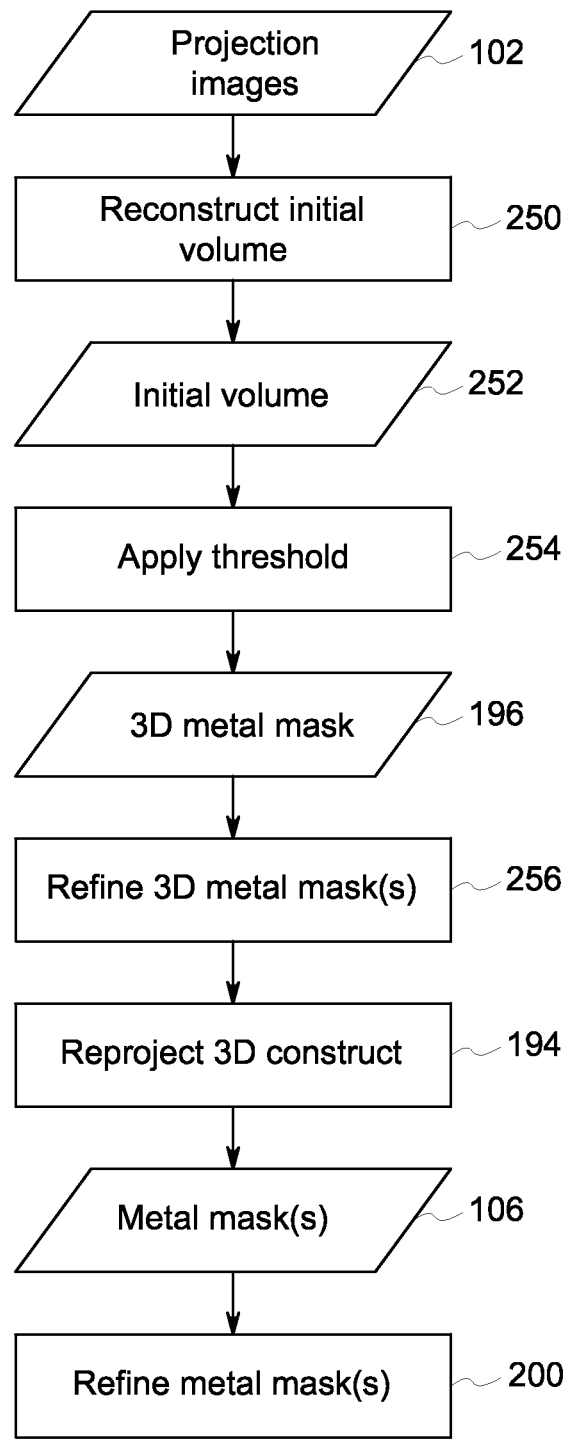
FIG. 5 depicts a flowchart depicting alternative algorithmic steps for generating metal masks, in accordance with aspects of the present disclosure.

Alternatively, turning to FIG. 5, in a different implementation the metal mask(s) 106 may be identified using an initial reconstruction (block 250), such as an analytical reconstruction (e.g., filtered backprojection) of the projection images 102. In one example a 3D metal mask 196 is identified through appropriate thresholding (block 254) of an initially reconstructed volume 252. In certain implementations, the threshold may be locally adapted, such as based on local penetration through the background composition. For example a smoothly varying threshold as a function of z-location may be implemented. In one such example, a modeled or expected anatomy or structure may be employed as part of this process. For instance, a model of the spine (or whatever the imaged anatomy or structure is) may be used to model the variation of the "natural" attenuation due to the imaged anatomy (e.g., in the z-direction), and thresholds chosen accordingly.

In the case where metal is present in the imaged volume the metal typically exhibits a "blooming" characteristic in the reconstructed volume 252, which may make it difficult to select an appropriate threshold that encompasses the metal, with only small deviations from the true metal volume. In addition, for limited-angle data (such as may exist for a C-arm or mobile C-arm imaging system), the axial cross-section of the backprojected metal structure may not be rotationally symmetric (even when the metal structure has a circular cross-section), thereby making it difficult to select an appropriate threshold, even manually. A similar effect is caused by varying degrees of data consistency. For example, inconsistencies may be caused by beam hardening, i.e., varying "penetration" of the X-ray through the metal or by varying X-ray techniques throughout the scan, and so forth.

In one embodiment, a refinement step 256 may be performed after the 3D metal mask 196 is created through an appropriate thresholding or segmentation step. The refinement step 256 may use similar approaches as the step used to combine the tentative 2D metal masks 184 into a combined 3D metal mask 196 discussed with respect to FIG. 4. Similarly, in this approach, for example, image locations that correspond with high confidence to background locations (i.e., where there is no metal present), may be used to refine the 3D metal mask 196, e.g., by removing any corresponding locations from the 3D metal mask 196, before reprojecting the 3D metal mask (in step 194) to obtain metal masks 106 in the projection domain. Such an approach allows the implementation to be robust even in instances where there are limitations in the data quality and minimizes problems associated with metal masks that are selected too small or too large, as discussed above.

The preceding discussion with respect to FIGS. 4 and 5 describe two different approaches for deriving metal masks 106 in the projection domain. The metal masks 106, regardless of the manner in which they are derived, may benefit from additional processing (block 200) in the projection domain to clean or refine the masks. In certain embodiments, these steps generally refine the boundaries of the metal regions (e.g., in this step pixels that correspond to metal but which were not included in the metal mask 106; or, conversely, pixels that were included in the metal mask 106 but belong to the background are relabeled if they are close to the boundary of an existing/identified metal region).

To avoid creating a large number of false positives (i.e., pixels labeled as metal when in fact they do not correspond to a metal location) for each individual projection image (as may occur with the tentative metal masks 184), certain of the steps discussed herein are focused on identifying the boundary of the metal masks by growing or shrinking the reprojected metal masks 106, where the associated pixels in the image can be easily identified using appropriate morphological dilation/erosion steps, and updating labels only in the boundary region, while other image regions are ignored. Without this restriction to growing/updating regions that are part of the boundary, i.e., in the immediate neighborhood of the existing metal masks 106, there is a potential for wide areas, e.g., of bone surfaces, to be erroneously added in the metal masks 106. In one implementation, a clean-up step as discussed herein is performed as a sequence of consecutive steps, where each step evaluates the option of growing or shrinking the regions by one pixel, for example. In each step, boundary pixels are identified, and their respective labels are updated, as discussed herein below.

Similarly as in the creation of the tentative metal masks 184, one option for the refinement of the metal masks 106 is to use a "threshold over background" approach. In such implementations, knowledge and/or assumptions about metal regions can be leveraged to create a refined background image that is cleaner (relative to the background image 188 that may be used in the creation of the tentative metal masks 184 in certain embodiments) in that it eliminates or otherwise accounts for a significant fraction of pixels that have already been determined to be metal pixels.

Figure 6:
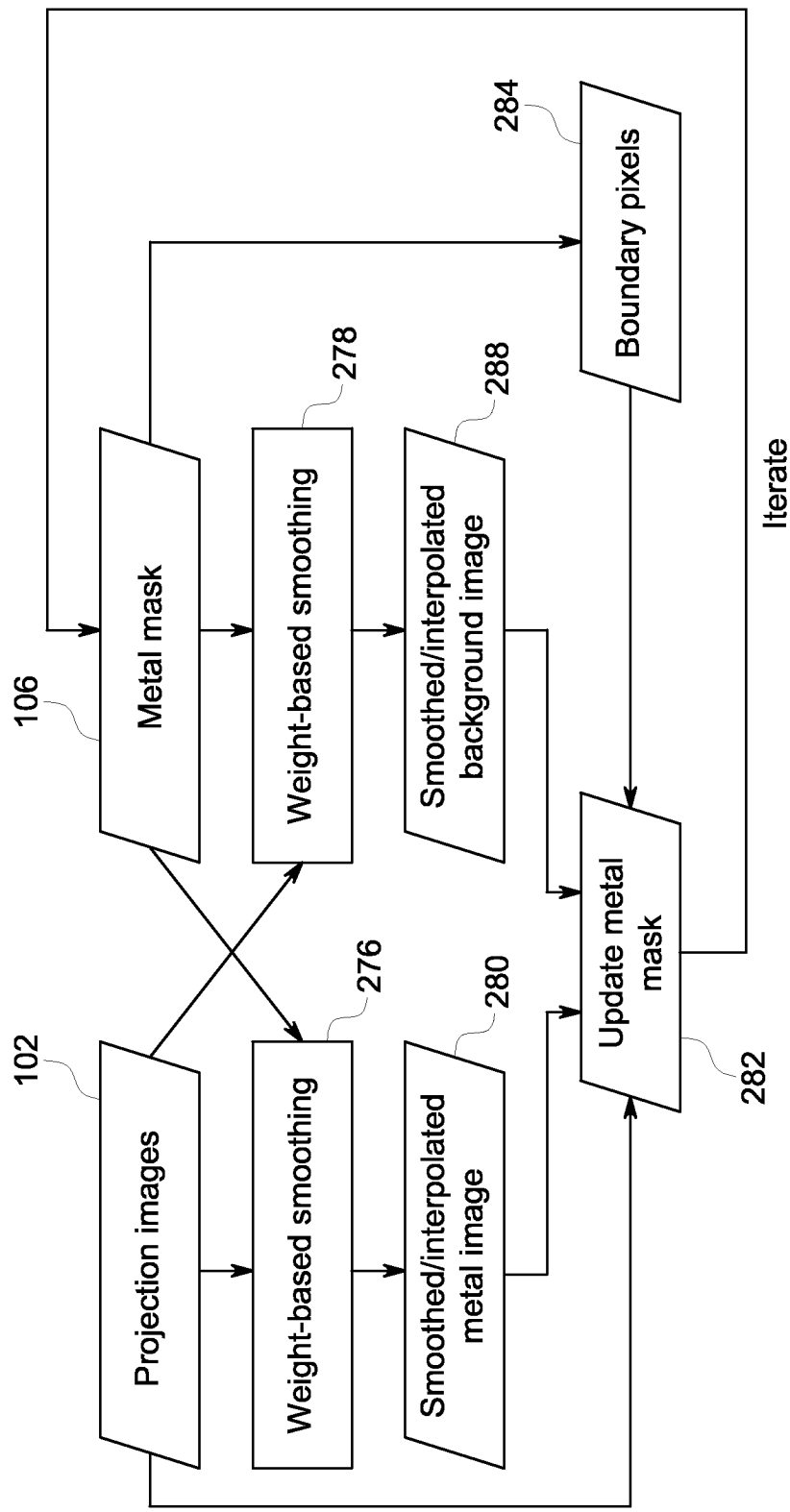
FIG. 6 depicts a flowchart describing algorithmic steps for refining metal masks, in accordance with aspects of the present disclosure.

Turning to FIG. 6, in one embodiment, a refined background image 288 may be obtained by applying (block 278) a weight-based smoothing operation, using an appropriate weighting function that is derived from the current metal mask 106. The threshold over background approach may be used to update the "background" or "metal" labels in the boundary regions 284 of the metal masks 106, thereby growing and/or shrinking the metal masks 106 in one or more consecutive or iterated update steps (block 282). For example, if a pixel within the identified boundary region that is currently labeled as "background" exceeds the local metal threshold (given by background plus some delta), the associated label is updated to "metal". Conversely, if a pixel is labeled as "metal" and its value is below the local threshold, its label is updated to "background". These updates may then be applied to the metal mask 106 to refine or clean the metal mask 106 and the process may be repeated (i.e., iterated) a set number of times or until a convergence criterion is satisfied.

Similarly, in another implementation, information about the locally estimated signal level in the metal regions may be used as additional information in order to classify the pixels as being either "background" or "metal". In order to estimate the metal signal level, and in the example depicted in FIG. 6, weight-based smoothing (block 276) may also be applied to update or generate a smoothed or interpolated metal image 280 based on the respective projection image 102 and metal mask 106. In this embodiment, the local metal signal value (which is represented by the smoothed/interpolated metal image 280) is determined using a weight-based local averaging operator, as discussed above, where the weights are set to zero in the background region, and 1 in the metal region. This information may be used in addition to the estimate of the local background signal level, discussed above. In one embodiment, the threshold for this classification (i.e, the update of labels associated with pixels in the boundary region) may be based on a value between the local background signal values and the local metal signal values, such as the value halfway between these values. Alternatively, in an attempt to minimize the number of pixels that may create streak artifacts in the final reconstructed image and/or in order to take into account partial voluming effects, (e.g., focal spot blurring, and so forth), the threshold for classification may be chosen to be closer to the "background value" than the "metal value".

When using this strategy it may be advantageous to update the local metal value after each update step 282, thereby obtaining a more realistic local metal signal value after each iteration. For example, this may be advantageous to the extent that the metal masks 106 may include at least some background pixels, such as due to dilation of the tentative metal masks 184 before the backprojection (block 192), in combination with the fact that in most cases the metal structures will be relatively small. The background signal may generally be considered more stable, such as due to averaging being generally performed over larger regions (and therefore the relative impact of a few metal pixels is smaller). Further, greater stability of the background signal may also be observed because the background signal may already be based on a dilated metal mask, thereby increasing the likelihood that there are no metal pixels contained in the considered region. By computing the background signal in this way it does not need to be re-computed at each iteration of the metal mask refinement, thereby reducing computational complexity.

Certain of the approaches discussed herein for identifying the metal mask(s) 106 in the projection images 102 focus on low-level image processing operations (i.e., thresholding operations, dilation and expansion operations and so forth). Alternatively, more complex approaches, e.g., using explicit shape models/constraints, and so forth, may be used. However, such complex approaches may be more computationally expensive than other approaches discussed herein.

Figure 7:
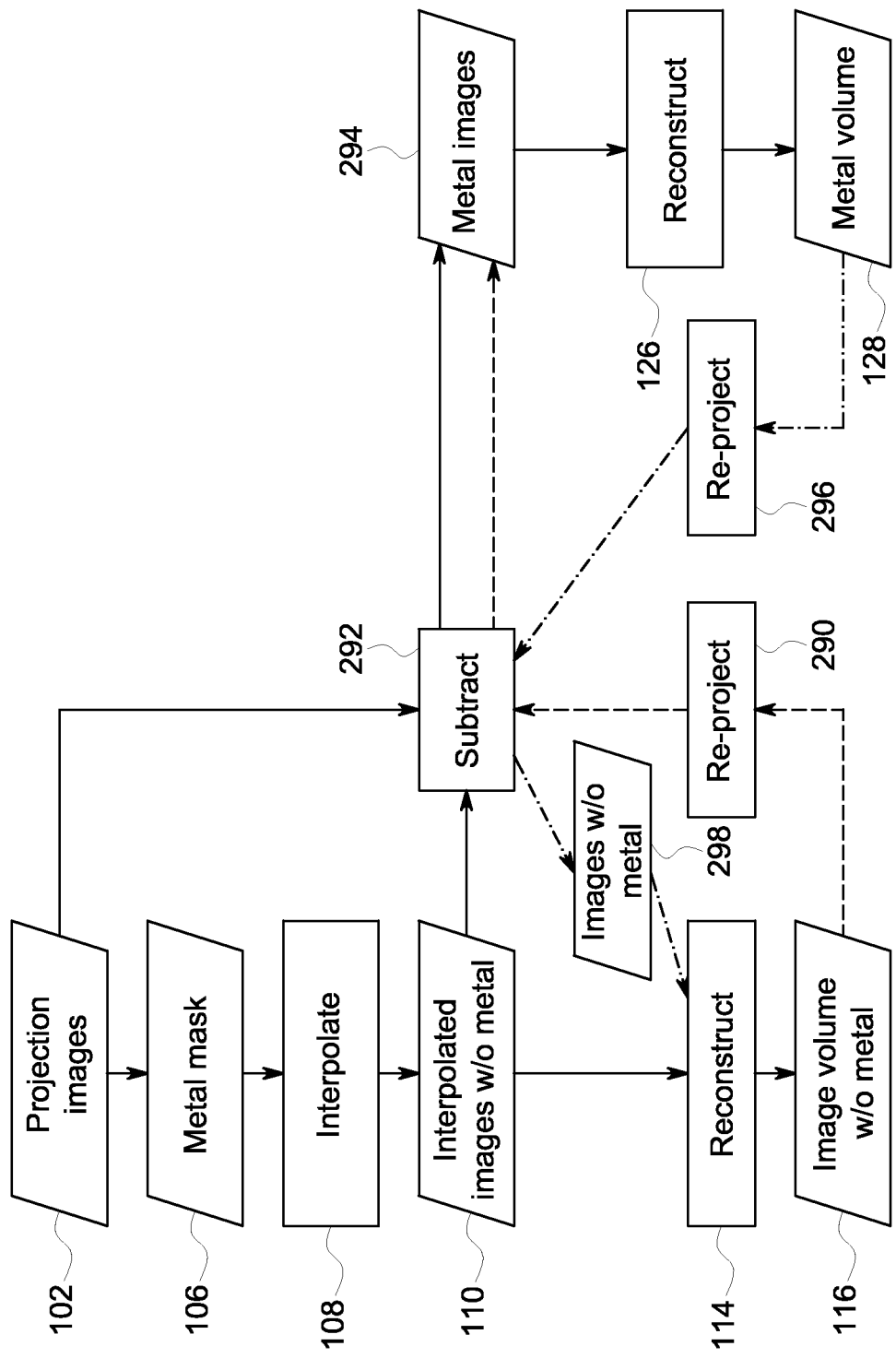
FIG. 7 depicts a flowchart describing algorithmic steps for processing projection images to generate a background volume and a metal volume, in accordance with aspects of the present disclosure.

Turning to FIG. 7, once the metal masks 106 are determined in projection space, an interpolation step (block 108) is performed to interpolate the projection image data 102 based on the metal masks 106. In this step, data corresponding to the identified metal masks 106 in the projections 102 is replaced with interpolated values. In one embodiment, the interpolation is based on data outside of the respective metal masks 106, e.g., by using the weight-based local averaging operator discussed above. In this way data may be obtained within the metal region that represents a local average, based only on values in the background region. After this step, the pixel values in the metal region of the original projection images 102 (as defined by metal masks 106) may be replaced by the corresponding pixel values in the smoothed image, thereby creating an interpolated image 110 where the pixel values corresponding to the metal mask 106 are replaced by a local average of background pixel values.

For the interpolated data to properly represent local data (which may be desirable to minimize contrast between the interpolated metal regions and the background), the smoothing kernel used should have a footprint that is not too large. However, this goal should be balanced against the risk that the kernel may not be sufficiently large to provide interpolated data across the full metal region, if the metal object is large. In this circumstance, the above steps may be performed so as to first replace pixels within the metal region, where the averaging operator is based on a pre-determined minimum number of pixels (or combined weights) from the background region (e.g., only pixels where the interpolated value is based on at least half the pixels within the footprint of the averaging kernel). The same step may then be repeated until all pixels within the metal region have been replaced with an interpolated value.

It may also be desirable to smooth the final interpolated image 110 with a smoothing operator, such as a small size smoothing operator, and replace the interpolated image values within the metal mask regions with the smoothed values. This step, when performed, may help minimize remaining edges between interpolated values within the metal mask 106 and the background, which may be useful since these image edges tend to contribute to artifacts in the reconstructed image. In this smoothing step, a limited number of pixel values outside of the metal mask 106 may also be replaced. In one example, a weighted average between true pixel value and smoothed pixel value is chosen, where the relative weight of the smoothed pixel value decreases as a function of distance from the metal mask 106.

Other approaches for providing interpolated image values within the metal regions may also be employed. These approaches include, for example, PoissonCloning. In another embodiment, the interpolation step 108 may be skipped and the corresponding pixels in the data labeled as "no data available" regions, which are defined by the set of mask images 106. These pixels can then be taken into account accordingly in the subsequent reconstruction step. In yet another approach, the high contrast part of the metal region is removed, while some of the image detail in the metal regions is preserved. This can be achieved, for example, by adding image detail in the metal region (in some instances weighted with an appropriate factor) back to the interpolated image (which does not contain any image detail in the interpolated region); and the detail in the metal region may be obtained by subtracting a smoothed version (e.g., obtained with the weight-based averaging) of the image in the metal region from the original image.

Turning back to FIG. 1, as will be recalled, a reconstruction step (block 114) is performed to generate an image volume 116 that is free of or has reduced metal artifacts (i.e., a background volume). For example, in one implementation, based on the interpolated projection image data 110, a 3D reconstruction (e.g., volume 116) that is free (or substantially free) of metal and is representative of the background is generated. The reconstruction may be an analytic reconstruction (e.g., a filtered backprojection), an iterative reconstruction (e.g., where reconstruction steps are updated and iterated (such as based on modeled or expected values) until a cost or completion function is satisfied), or a combination of these approaches (e.g., filtered backprojection followed by iterative updates). In an iterative (or hybrid) reconstruction approach, as described herein, there may be operators that are applied at each iteration step, or only at some iteration steps (e.g., total variation minimization, or a step in the direction of the gradient of the total variation). The purpose of these operators may be to mitigate noise, streak artifacts, and so forth. In the context of the present approach, such operators may be applied selectively (e.g., only within the metal mask 106 or only outside the metal mask 106), or with locally different weighting, and so forth. The reconstruction step 114 therefore generates a background image volume 116 that is free of or has reduced artifacts due to the metal objects within the imaged volume. For example, in one embodiment, streaks due to metal tools and so forth are reduced or eliminated.

An additional step may be performed whereby the metal structure(s) are added (block 118) to the background image volume 116 to generate a final volume 120. In one implementation the metal information is inserted into a streak-free volumetric image 116 obtained previously. In one embodiment, the metal information (e.g., metal structure) may be obtained by performing a reconstruction step based on residual projection images, such as where the residual projection images are obtained as the difference between the original projection images and the interpolated projection images.

With the foregoing in mind, and turning back to FIG. 7, this figure depicts a variety of approaches that may be employed to generate and/or further process the metal-free volume 116 (i.e., the "background" image volume) and the metal volume 128 discussed with respect to FIG. 1. For example, in one set of implementations (denoted by the solid arrows) both the background and metal reconstruction may be processed "in parallel" to derive the respective background volume 116 and metal volume 128 separately from one another. In a variation of this approach, (denoted by the dashed arrows) the "background" (i.e., the metal-free volume 116) may be reconstructed first and reprojected (block 290). The difference (subtraction block 292) may then be obtained between the reprojection of the metal-free volume 116 and the original projection images 102 and the resulting metal images 294 may then be used to reconstruct the metal volume 128. In a further variation (denoted by the dash-dotted arrows) the metal volume 128 may be reconstructed (block 126) first and reprojected (block 296). The reprojected metal volume may be used to obtain a difference (subtraction block 292) relative to the projection images 102, thereby creating metal-free projection images 298, which may in turn may be used to reconstruct (block 114) the background volume 116.

Similarly, in addition to those variations depicted, a set of hybrid or composite options are available in which different aspect of these approaches are combined, utilized, or iterated at different points or times. It may also be noted that, since the second and third option noted above (denoted by the dashed and dash-dotted arrows) conceptually represent a reprojection of some "initial estimate" of one of the volumes of interest, and then proceeding to reconstruct a residual signal, there is also an option where the two volumes (i.e., background volume 116 and metal volume 128) are not kept separate and, instead, one of these volumes may serve as an initial estimate of an iterative reconstruction of the remaining elements.

In certain approaches, the residual images consist of the residual images between the reprojected "streak-free" volume 116 (as opposed to the interpolated images 110) and the original projection images 102. For iterative updates, either one of these differently calculated types of residual images, or a weighted combination of the differently calculated types of residual images may be used. In such embodiments, the different types of residual images may be used at different stages in the reconstruction. In one embodiment, the reconstruction (block 126) of the metal structure 128, and combination of the two volumes (i.e., metal structure 128 and image volume 116), is followed by one or more additional joint reconstruction or update steps.

In yet another implementation, the 3D metal image is reconstructed first, followed by a reconstruction based on the residual images where the residual images are based on the difference between original projection images 102 and the reprojected metal volume, i.e., metal masks 106. In such an implementation, the metal image 294 (as discussed here) represents the delta (in attenuation) of the metal over the local background, and not the true 3D metal structure.

As will be appreciated, the sequence of the discussed steps may be modified, steps may be combined, and/or may be performed multiple times (i.e., iterated). For example, in one embodiment the reconstruction (block 126) of the metal structures 128 and the reconstruction (block 114) of the background (i.e., image volume 116) are performed in alternating steps, with each step further refining the result.

Turning now to the reconstruction of the metal volume 128, depending on the data quality, some data may be processed so as to minimize the generation of streaks. For example, the residual images (e.g., metal images 294) may be clipped (to limit the image contrast of high contrast structures), or scaled, and so forth. This processing may also encompass processing steps using information related to the forward projected metal mask, e.g., high values near the edge of the metal region in the residual projection images may be suppressed more than values that are farther away from the edge of the metal mask 106.

In one implementation, residual projection images are generated by determining the difference images between the original projection images 102, and the interpolated images 110. In such an implementation, the residual images are essentially non-zero only in the metal regions of the projection images 102 (i.e., are metal images 294). Based on the residual images, here metal images 294, a simple backprojection (block 126) may be performed. In this manner, a 3D volume (e.g., metal structure or volume 128) is created with high contrast at the true location of the imaged metal objects, in combination with streaks with somewhat lower contrast. In certain embodiments a soft-thresholding step may be employed so that the relative contrast between metal regions and the streaks within the background region may be improved. By way of example, a soft thresholding step may be employed that replaces a value x by $f(x)=sign(x)*max([abs(x)-d, 0])$, where d represents the threshold value. The threshold value may, in one embodiment, be set equal to the maximum value of the reconstructed metal value outside of the 3D metal mask 196, thereby completely eliminating the streaks. Alternatively, the threshold value may be set to some scaled version of the maximum value outside of the metal mask, thereby retaining some of the more gradual characteristics of the reconstructed metal. In one embodiment, the threshold may be chosen similarly to what is discussed above, but constrained to a region near the center of the field of view. In this manner, artifacts related to the edge of the acquired images or FOV may be avoided or reduced. Examples of other suitable approaches for managing the streak artifacts induced by the metal structures 128 include, but are not limited to, order statistics-based approaches or weight-based backprojection.

In some instances, due to the soft-thresholding step, the reconstructed volume (i.e., metal structure 128) may retain only the highest contrast objects or the most high-contrast parts of the metal objects. That is, some metal structures may not appear in the reconstruction. This issue may be addressed by combining this approach with a clipping of the residual data (e.g., metal images 294) before the reconstruction (block 128). For example, in one embodiment, the clipping step replaces a value x with $f(x)=sign(x)*min([abs(x), d])$, where d is the clipping threshold. Another strategy to address this issue consists of locally scaling and/or adding a constant to the residual image such as to achieve a constant local mean. In one such implementation, the scaling and/or additive components are locally smooth.

The reconstructed metal structure 128 may have a smaller contrast than the true metal structures in the image. This may be due to two factors: the typically small size of the metal structures (simple backprojection distributes the contrast over the full ray path, i.e., the contrast in the simple backprojection is not appropriately scaled) and the soft-thresholding operation, which lowers the contrast. Therefore the reconstructed metal structure 128 may be scaled with an appropriate constant factor before being combined (block 118 of FIG. 1) with the generally "streak-free" reconstructed image volume 116. The appropriate scaling factor may also be chosen by forward projecting a binary 3D metal mask, and using the obtained pathlengths (with or without appropriate local smoothing) as suitable local scaling factors. A further improvement in contrast and quality of the representation of the metal structure 128 may be obtained by iteratively updating the reconstructed metal image.

A further option may be to combine the metal structure reconstruction (block 126), as described herein, with the application of a modified ramp filter (e.g., a modified ramp filter as used in filtered backprojection reconstruction in CT), thereby achieving a better contrast of the reconstructed metal structures 128 corresponding to the metal object. Hybrid combinations of filtered backprojection and iterative update may be used as well.

In one embodiment, any one of the above approaches to reconstruct a volumetric image (i.e., metal structure 128) representing the 3D metal structure may be combined with an appropriate masking of the reconstructed metal structure 128 using the 3D metal mask (e.g., using a multiplication with the binary 3D metal mask 196), instead of or in combination with the soft-thresholding step. However, the soft-thresholding approach may lead to a more accurate representation of metal edges due to appropriate handling of image information from pixels that were erroneously labeled as metal. In one embodiment, the 3D metal structure 128 is created by scaling the 3D metal mask 196 with an appropriate constant value.

Yet another embodiment may include a forward projection of the binary metal mask in order to estimate the pathlength (through the metal mask) at each point in the projection image 102. The image information representing the metal structure may then be normalized (e.g., by dividing by the pathlength on a pixel-by-pixel basis) and this information backprojected into the metal mask. Subsequently, the backprojections from all projections may be averaged. This approach may be used in combination with one or more of a suitable iterative update, masking with the 3D metal mask 196, soft thresholding, and/or appropriate scaling.

In a final processing step, the reconstructed "metal-free" image volume 116 and the 3D metal structure 128 are combined, e.g., by summation (block 118 of FIG. 1). Further, in one embodiment, the values in the metal structure 128 may be scaled to facilitate optimized viewing of the reconstructed dataset (i.e., volume 120 of FIG. 1). In one example, the contrast of the metal structure 128 may be scaled down such that the metal region is not saturated when displaying the volume 120, while still leaving the structure and details of the metal visible. In such an embodiment, the contrast scaling of the metal structure 128 may also be performed so that the visibility of the imaged anatomy is improved or otherwise remains suitable.

Technical effects of the invention include minimizing artifacts due to metal structures in reconstructed 3D images from an X-ray system. The presently contemplated approaches address limitations that may be encountered with certain types of imaging systems, such as mobile C-arm systems. These limitations that are addressed may include limited angle acquisition, small number of views, image truncation, limited quantitative resolution, limited X-ray penetration, and so forth. The technical advantages of the presently disclosed approaches include, but are not limited to, the reduction or elimination of metal artifacts in images in a computationally robust and fast manner. These advantages include improved image quality, reduction of streaks due to metal, and improved representation of metal structures.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for processing projection image data, by way of a processing component, the method comprising:
providing an image processing system comprising a memory storing one or more routines and the processing component configured to execute the one or more routines stored in the memory, wherein the one or more routines are executed by the processing component;
accessing or acquiring projection image data from the image processing system;
generating a set of tentative two-dimensional (2D) metal masks, wherein each tentative 2D metal mask is generated based on a comparison between a respective projection image and a corresponding background image;
backprojecting each tentative 2D metal mask to generate a respective set of backprojected three-dimensional (3D) data in image space for each tentative 2D metal mask;
combining the sets of backprojected three-dimensional (3D) data in image space to generate a 3D metal mask; and
reprojecting the 3D metal mask to generate one or more metal masks in projection space.

2. The computer-implemented method of claim 1, wherein each corresponding background image is generated by performing a weight-based smoothing of the respective projection image using a respective weight image.

3. The computer-implemented method of claim 2, wherein each respective weight image is derived from a label image corresponding to the respective projection image.

4. The computer-implemented method of claim 3, wherein each corresponding background image is iteratively generated or updated based on updates to the respective label image after each iteration.

5. The computer-implemented method of claim 1, wherein generating the 3D metal mask comprises, at each voxel within the combined backprojected 3D data, determining how many tentative 2D metal masks show non-metal data at each voxel location and how many tentative 2D metal masks show the presence of a metal object at each voxel location, wherein the tentative 2D metal masks may be weighted or unweighted.

6. The computer-implemented method of claim 1, wherein generating the 3D metal mask comprises determining, using a set of confidence weights, a confidence-weighted sum of the respective backprojected tentative metal masks at each voxel location and determining the sum of backprojected confidence-weights at each voxel location.

7. The computer-implemented method of claim 6, wherein the confidence weights used in determining the confidence weighted sums are binary.

8. The computer-implemented method of claim 6, wherein the confidence weights for each respective projection are derived from the local penetration or signal level in the corresponding background image.

9. The computer-implemented method of claim 6, wherein the confidence weights for each respective projection are derived from a measure of confidence in a tentative metal label.

10. The computer-implemented method of claim 6, wherein the confidence weights for each respective projection are derived from prior knowledge of a collimator position with the respective projection image.

11. The computer-implemented method of claim 6, wherein the confidence weights for each respective projection are derived from prior knowledge of data points being invalid in portions of the projection image.

12. The computer-implemented method of claim 6, wherein a voxel within the 3D metal mask is characterized as metal if the ratio of confidence weighted sums of the backprojected tentative 2D metal masks to the sum of the confidence weights exceeds a threshold that is less than 1.

13. The computer-implemented method of claim 1, comprising expanding or dilating the tentative 2D metal masks prior to backprojection.

14. The computer-implemented method of claim 1, comprising refining the one or more metal masks in projection space.

15. An image processing system, comprising:
a memory storing one or more routines; and
a processing component configured to execute the one or more routines stored in the memory, wherein the one or more routines, when executed by the processing component, cause acts to be performed comprising:
accessing or acquiring projection image data;
generating a set of tentative two-dimensional (2D) metal masks, wherein each tentative 2D metal mask is generated based on a comparison between a respective projection image and a corresponding background image;
backprojecting each tentative 2D metal mask to generate a respective set of backprojected three-dimensional (3D) data in image space for each tentative 2D metal mask;
combining the sets of backprojected three-dimensional (3D) data in image space to generate a 3D metal mask; and
reprojecting the 3D metal mask to generate one or more metal masks in projection space.

* * * * *